US00RE35552E

United States Patent [19]

Lankinen

[11] E Patent Number: Re. 35,552

[45] Reissued Date of Patent: Jul. 8, 1997

[54] DEVICE INTENDED FOR MEASURING A DOSE OF POWERED MEDICAMENT FOR INHALATION

[75] Inventor: Tapio Lankinen, Turku, Finland

[73] Assignee: Leiras Oy, Turku, Finland

[21] Appl. No.: 343,930

[22] PCT Filed: Apr. 15, 1991

[86] PCT No.: PCT/FI91/00113

§ 371 Date: Feb. 16, 1993

§ 102(e) Date: Feb. 16, 1993

[87] PCT Pub. No.: WO92/18188

PCT Pub. Date: Oct. 29, 1992

Related U.S. Patent Documents

Reissue of:

[64] Patent No.: 5,295,479
Issued: Mar. 22, 1994
Appl. No.: 955,743
Filed: Apr. 15, 1991

[51] Int. Cl.[6] ..... A61M 15/00

[52] U.S. Cl. ..... 128/203.12; 128/203.15

[58] Field of Search ..... 128/200.14, 203.15, 128/203.21, 203.12; 604/58

[56] References Cited

U.S. PATENT DOCUMENTS

| | | | |
|---|---|---|---|
| 31,530 | 2/1861 | Cluxton | 222/352 |
| 68,760 | 9/1867 | Lipe | 222/352 |
| 137,093 | 3/1873 | Pinchard | 128/203.15 |

(List continued on next page.)

FOREIGN PATENT DOCUMENTS

| | | | |
|---|---|---|---|
| 0407028 | 1/1991 | European Pat. Off. . | |
| 79947 | 12/1989 | Finland . | |
| 1503827 | 8/1989 | U.S.S.R. | 128/203.15 |
| 704167 | 2/1954 | United Kingdom | 128/203.21 |
| 2165159 | 4/1986 | United Kingdom . | |

OTHER PUBLICATIONS

Derwent Publications Ltd., Abstract No. 90–073613/10 (SU 1503–827–A), Publication Week 9010 (Gorki Paediatrics).

PCT No. WO 92/04068, Publ. Mar. 19, 1992, Poss et al., "Inhalator Without Propeller Gas With Foreign Air Stream", Abstract of Patent.

PCT No. WO 89/01348, Publ. Feb. 23, 1989, Ikura et al., "Powdery Medicine Applicator Device", Abstract of Patent.

PCT No. WO 92/00771, Publ. Jan. 23, 1992, Braithwaite et al., "Inhaler", Abstract of Patent.

EP No. 0 451 745 A1, Publ. Oct. 16, 1991, Chiesi et al., "Device for the Administration of Powdered Medicinal Substances", Abstract of Patent.

EP No. 0 520 440 A1, Publ. Dec. 30, 1992, Ambrosio et al., "Inhalation Device for Powdered Medicaments", Abstract of Patent.

PCT No. WO 92/09322, Publ. Jun. 11, 1992, Gupte et al., "Inhalation Device", Abstract of Patent.

PCT No. 93/03782, Publ. Mar. 4, 1993, Del Bon et al., "Inhaler", Abstract of Patent.

*Primary Examiner*—Aaron J. Lewis
*Attorney, Agent, or Firm*—Rothwell, Figg, Ernst & Kurz

[57] ABSTRACT

The invention relates to a device intended for measuring a dose of powdered medicament for inhalation, including a medicament container (1), through which extends a shaft (3) provided with at least one dosage recess (5). Container (1) is provided with at least one flap-like sweeper element (4), resting on shaft (3) in alignment with the dosage recess and having one of its ends rotatable around shaft (3), the other end of said flap dragging along the shaft surface, whereafter said shaft (3) is displaceable in this longitudinal direction relative to container (1) so as to bring dosage recess (5), along with a dose of the medicament carried therein, outside container (1). The invention relates also to the measuring of a dose of powdered medicament for inhalation by using the device described above.

12 Claims, 5 Drawing Sheets

U.S. PATENT DOCUMENTS

Figure 1:
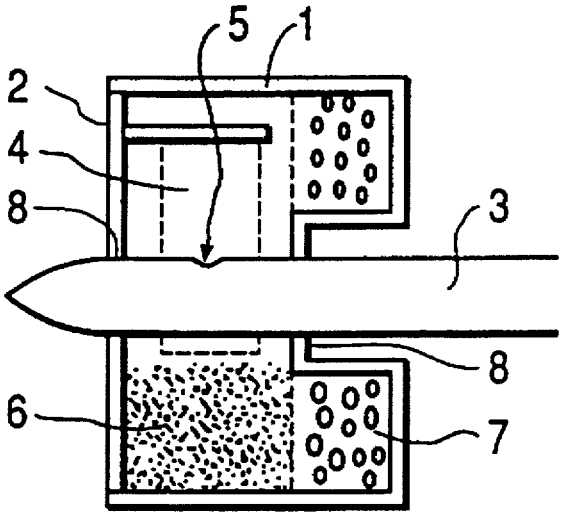

| | | | |
|---|---|---|---|
| 202,625 | 4/1878 | Avery | 222/348 |
| 2,534,636 | 12/1950 | Stirn | 128/203.15 |
| 2,590,832 | 3/1952 | Brown | 128/203.15 |
| 2,603,215 | 7/1952 | Arnow | 128/203.15 |
| 3,029,002 | 4/1962 | Gregoire | 222/368 |
| 3,204,833 | 9/1965 | Weidzner | 222/368 |
| 4,046,146 | 9/1977 | Rosskamp et al. | 128/203.15 |
| 4,047,525 | 9/1977 | Kulessa et al. | 128/203.15 |
| 4,084,729 | 4/1978 | Epple | 222/307 |
| 4,274,403 | 6/1981 | Struve | 128/203.15 |
| 4,446,862 | 5/1984 | Baum et al. | 128/203.15 |
| 4,524,769 | 6/1985 | Wetterlin | 128/203.15 |
| 4,570,630 | 2/1986 | Elliott et al. | 128/203.15 |
| 4,576,157 | 3/1986 | Raghuprasad | 128/200.23 |
| 4,709,837 | 12/1987 | Erdman | 222/636 |
| 4,805,811 | 2/1989 | Wetterlin | 222/337 |
| 4,907,583 | 3/1990 | Wetterlin et al. | 128/203.15 |
| 4,940,051 | 7/1990 | Lankinen | 128/200.18 |
| 5,033,463 | 7/1991 | Cocozza | 128/203.21 |
| 5,069,204 | 12/1991 | Smith et al. | 128/200.23 |
| 5,070,870 | 12/1991 | Pearce | 128/203.15 |
| 5,113,855 | 5/1992 | Newhouse | 128/203.12 |
| 5,161,524 | 11/1992 | Evans | 128/203.15 |
| 5,201,308 | 4/1993 | Newhouse | 128/203.15 |
| 5,239,991 | 8/1993 | Chawla et al. | 128/203.15 |
| 5,239,992 | 8/1993 | Bougamont et al. | 128/203.15 |
| 5,239,993 | 8/1993 | Evans | 128/203.15 |
| 5,243,970 | 9/1993 | Ambrosio et al. | 128/203.15 |
| 5,287,850 | 2/1994 | Haber et al. | 128/203.21 |
| 5,301,666 | 4/1994 | Lerk et al. | 128/203.15 |
| 5,318,015 | 6/1994 | Månsson et al. | 128/200.22 |
| 5,318,016 | 6/1994 | Mecikalski | 128/200.23 |
| 5,320,093 | 6/1994 | Raemer | 128/203.12 |
| 5,320,094 | 6/1994 | Laube et al. | 128/203.12 |
| 5,320,095 | 6/1994 | Nijkerk et al. | 128/203.15 |
| 5,320,108 | 6/1994 | Cloutier | 128/716 |
| 5,320,258 | 6/1994 | Paul | 222/345 |
| 5,320,714 | 6/1994 | Brendel | 128/203.15 |
| 5,337,740 | 8/1994 | Armstrong et al. | 128/203.12 |
| 5,341,801 | 8/1994 | Zechner | 128/203.15 |
| 5,349,945 | 9/1994 | Wass et al. | 128/200.23 |
| 5,349,946 | 9/1994 | McComb | 128/203.17 |
| 5,349,947 | 9/1994 | Newhouse et al. | 128/203.21 |
| 5,351,683 | 10/1994 | Chiesi et al. | 128/203.12 |
| 5,355,872 | 10/1994 | Riggs et al. | 128/200.21 |

DEVICE INTENDED FOR MEASURING A DOSE OF POWERED MEDICAMENT FOR INHALATION

Matter enclosed in heavy brackets [ ] appears in the original patent but forms no part of this reissue specification; matter printed in italics indicates the additions made by reissue.

The present invention relates to a section of a powder inhalator required for the inhalation of a powdered medicament, said section containing powdered medicament as well as a mechanism required for measuring its dosage and delivering it out of a reservoir.

The dosage of a medicament for inhalation is generally effected by using a propellant-pressurized dosage aerosol or powder inhalator. With dosage aerosol, the metering of a dose is accurate based on the determination of liquid volume in a dosage valve with external moisture having no effect on the procedure. With powder inhalators, the metering is inaccurate for several reasons. Measuring or metering a dose is based on two prior known principles. The powder may be contained as measured portions in small dosage containers, e.g. capsules, from which it is metered and delivered into the inhalation air of a patient. A larger amount of powdered medicament can also be contained in a reservoir included in an inhalator, wherein a special mechanism is used for delivering a measured amount of powder into the inhalation air of a patient. Such multi-dosage inhalators are more convenient to a patient by virtue of their easy operation.

The medicament doses to be inhaled with powder inhalators may vary within the range of tenths of a milligram to tens of milligrams. The smaller the doses in question, the more difficult it is to effect a sufficiently accurate measuring of the dose and the greater a detrimental effect of extraneous disturbing factors on measuring accuracy. The most significant disturbing factor is external moisture . If a powdered medicament is moistened, e.g. during storage, it may form lumps for impaired measuring accuracy. The penetrability of moisture into a medicinal substance depends on the tightness of a medicament reservoir, the water-vapour permeability of a structural material as well as on the moisture absorbency of a medicament itself. It is prior known to alleviate the moisture trouble by means of a dehydrating agent associated with a medicament reservoir.

Moisture has also another effect on the accuracy of a medicament dose discharging from an inhalator. If those internal surfaces of an inhalator, which are in contact with discharging medicament powder, become moist, the delivered amount of medicament will be reduced to a fraction of the normal. The moistening may be a result of exhalation through an inhalator or of bringing the device from a cold place to a warm one. This moisture trouble could be inhibited by fitting the inhalator with a one-way valve preventing exhalation and other air-flows occurring through the device.

On the basis of what is stated above, a medicament reservoir and a dose measuring mechanism included in a multi-dosage inhalator should fulfil the following conditions:

- to measure at a sufficient accuracy both large and small doses
- have a structure as tight and compact as possible
- in terms of its structure, to facilitate the use of a one-way valve in the inhalator.

Further, in terms of total medication costs, it would be preferable to use a replaceable medicament reservoir.

Thus, with multi-dosage powder inhalators, the design of a medicament reservoir and a dose measuring mechanism is highly important not only in terms of dose measuring accuracy and stability of a powdered medicament but also a preferred inhalator structure. No prior art multidosage powder inhalator is provided with a medicament reservoir and a dose measuring mechanism that would fulfil all the above-mentioned conditions.

Finnish Patent publication No. 69963 discloses a multi-dosage dispenser provided with a medicament container and a dose metering device. The medicament container has a conical lower section and its bottom is provided with a shaft rotatable around its longitudinal axis. The shaft is fitted with one or a plurality of dosage recesses, into which the powder is flowing upon rotating said shaft. The container can be fitted with a dehydrating agent and a vibrator for an intensified flow of the powder upon rotating said shaft. After rotating the shaft through half a turn, the dosage recess has rotated so as to reach an inhalation conduit, which is located below the container and into which the powder drops.

The powdered medicament is well protected against moisture but it is required to have exceptionally good flowing or trickling properties for a uniform filling of the dosage recess. When using a design as described above, it is possible for a patient to receive an overdose of medicament if several loading actions are effected prior to inhalation. The medicament container is not replaceable, nor is there provided a one-way valve for blocking exhalation.

U.S. Pat. No. 4 046 146 discloses a multi-dosage inhalator, wherein the dose metering is effected by rotating a cylindrical medicament container having a perforated floor. The cylinder rotates around its center axis upon a fixed, circular bottom plate provided with a hole for dropping a dose into an inhalation conduit. As the medicament container is rotated, the holes in its floor are filled with a powdered medicament and wind up below a plate inside the container in alignment with a hole in the circular bottom plate, wherethrough the powder falls down gravitationally for inhalation.

The powdered medicament is poorly protected against moisture due to an extensive, untight sliding surface and a hazard of overdoses is ominous if several loading actions are effected prior to inhalation. Measuring of small doses is obviously inaccurate since gravity alone is not sufficient to cause a complete drop of the dose into an inhalation conduit. The design does not allow for effective use of a one-way valve. However, the medicament container is replaceable.

Finnish Patent publication No. 79947 discloses a multi-dosage inhalator, wherein the powder is packed in a medicament reservoir on a perforated sheeting and the perforated point of the sheeting is carried onto an inhalation conduit. In a commercially available device as set forth in this patent, the sheeting comprises a thin, circular plastic disc which, upon effecting a loading action, rotates into an inhalation conduit. The medicament reservoir is provided with a dehydrating agent. Despite the dehydrant, moisture will be able to affect the powdered medicament in time by way of wide and extensive sliding surfaces. The action of this device is troubled by a hazard of blocking the holes of a perforated plate and the sticking of medicament to the moist interior walls of an inhalation conduit. The medicament reservoir is not replaceable. The mechanism can be used to measure both small and large amounts of medicament.

In the present invention, the question is about a medicament container and a dose measuring mechanism for a multi-dosage powder inhalator for measuring or metering accurately both large and small medicament doses with the powdered medicament permanently and tightly protected from external moisture and for readily facilitating the use of a one-way valve for blocking exhalation through the powder inhalator as well as replaceability.

Operation of the device is based on filling a recess in a cross-sectionally circular shaft with an amount equivalent of a single dose of powdered medicament by rotating a shaft-surrounding medicament container around the shaft and in an inhalation conduit adjacent to the dose by pushing the shaft out of the medicament container. Filling of the recess is effected as a result of the gravity-induced powder rolling and by means of a sweeper element, fastened to the medicament container and leaning against the shaft. The sliding surfaces between shaft and medicament container are elastically tight.

A device of the invention is characterized in that the container is provided with at least one flap-shaped sweeper element, which rests upon the shaft in alignment with a dosage recess and one of whose ends is rotatable around the shaft, the other end of said flap dragging along the shaft surface, whereafter the shaft is displaceable in its longitudinal direction relative to the container so as to bring the dosage recess along with a medicament dose contained therein to a position below the container.

Figure 4A:
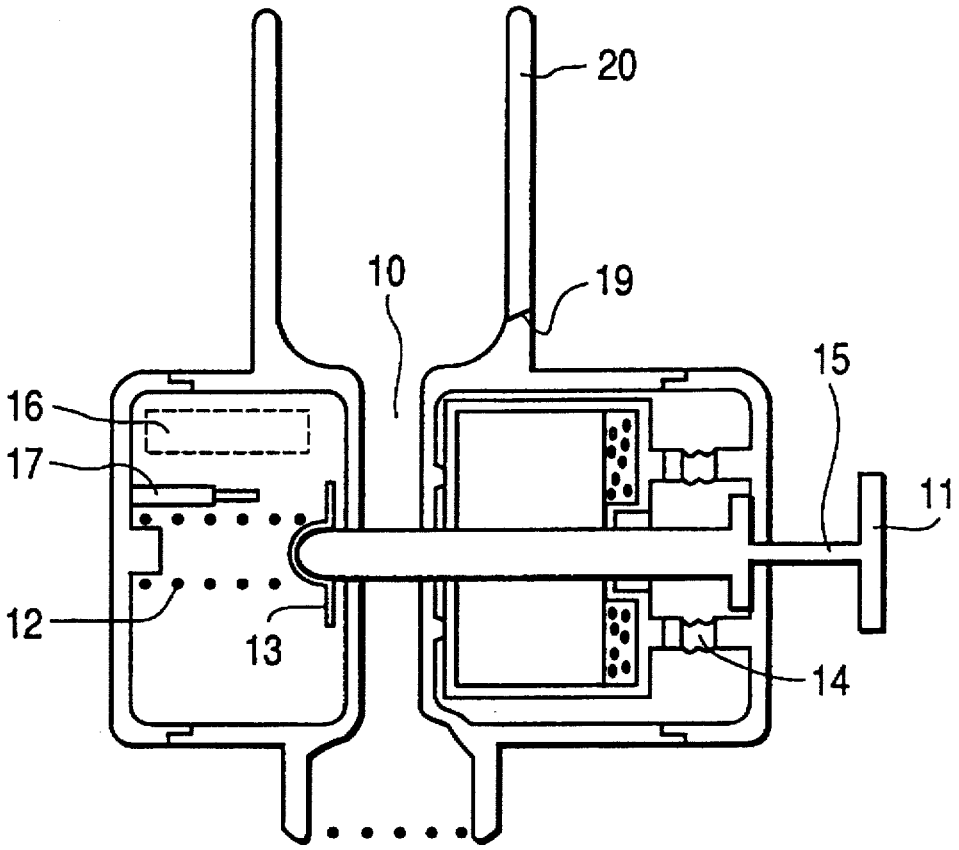
Figure 4B:
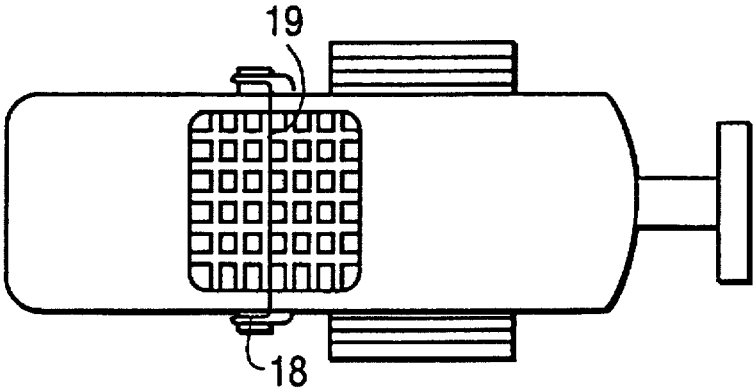
Figure 5:
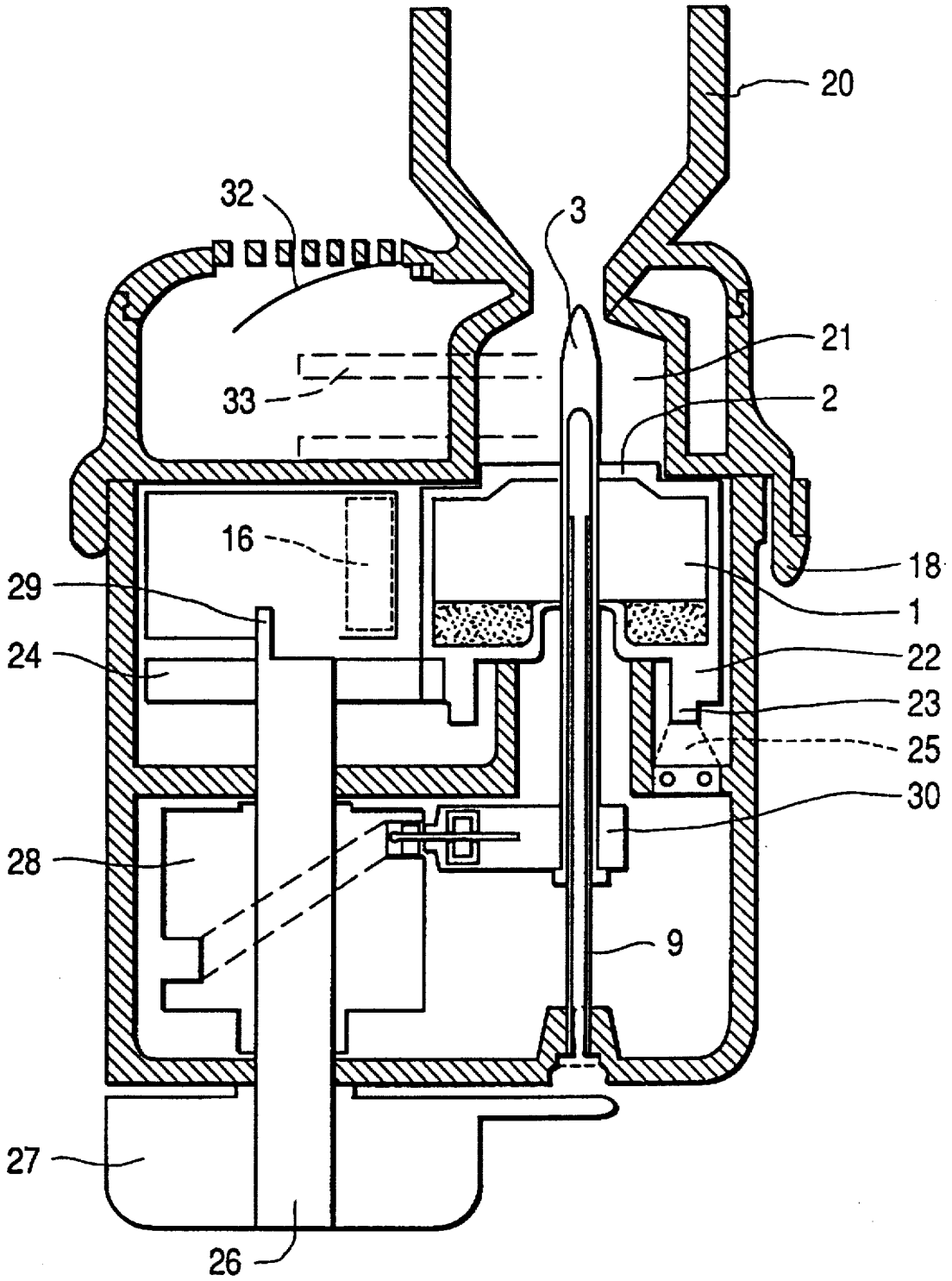

The invention will now be described in more detail with reference made to the accompanying drawings, in which FIG. 1 is a basic view of a device of the invention with a medicament container sectioned in the longitudinal direction of the shaft, FIGS. 2 a, b and c show the device of FIG. 1 in the longitudinal direction of the shaft, wherein the container is turned through a full rotation, FIGS. 3 a and b illustrate one embodiment according to the invention, FIGS. 4 a and b show an inhalation apparatus including a device of the invention, FIG. 5 illustrates another inhalation apparatus provided with a device of the invention, and FIGS. 6–9 show one modified embodiment of FIG. 5.

Referring to FIG. 1, the basic structure of a device is shown with a medicament container sectioned in the longitudinal direction of a shaft 3 and FIG. 2 shows it in a cross-section in the direction of the shaft. The device comprises a medicament container housing 1, a gable 2, a circular shaft 3 as well as a flap-shaped sweeper element 4 leaning against the shaft with a slight tension. In alignment with sweeper element 4, said shaft 3 is provided with a recess 5 for measuring a dose. A powdered medicament 6 lies freely on the floor of medicament container 1. Inside the container it is possible to place a dehydrating agent 7, packed e.g. as an annular body. Shaft apertures 8 are tight but allow for displacement of the shaft in its longitudinal direction. If necessary, there may be a plurality of dosage recesses 5 and those can be located in various parts of shaft 3. The number of sweeper elements 4 can also be more than one. The medicament container 1 has preferably a circular cross-section but other shapes are also possible. The shaft 3 is preferably located centrally in the medicament container but can also be located eccentrically.

Figure 2A:
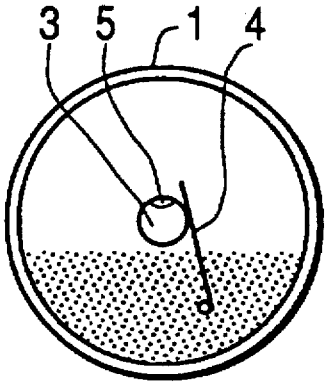
Figure 2B:
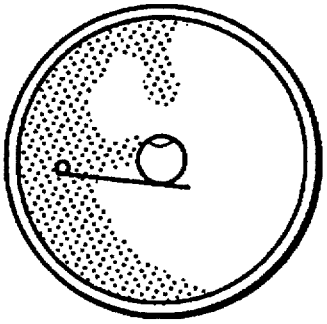
Figure 2C:
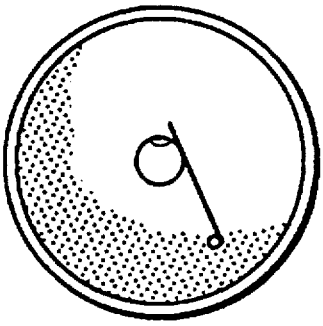

A dose measuring or metering procedure is illustrated in FIGS. 2a, b and c. Upon rotating the medicament container, the powdered medicament first (FIG. 2a) rotates along with the container but, upon continued rotation, it starts to trickle and fall downwards ending up on sweeper element 4 (FIG. 2b). As one rotation is completed, the sweeper element 4 has packed said dosage recess 5 full of powder with a slight tension (FIG. 2c). By pushing shaft 3 the dose can be displaced out of the container and simultaneously the tight shaft aperture 8 trims out a possible excess powder. As a strong gas flow (e.g. induced by inhalation) is directed to dosage recess 5, the latter is exhausted of the powdered medicament. The term "recess" refers to a depression, located in the shaft and having a volume that matches an individual dose of medicament.

Figure 3B:
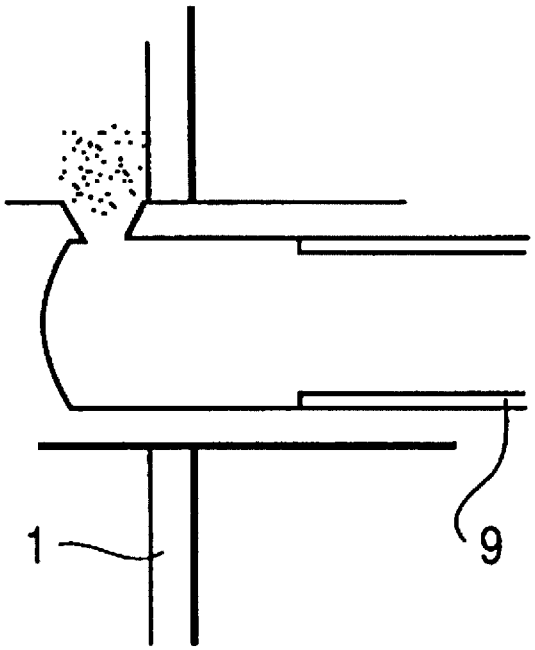
Figure 3A:
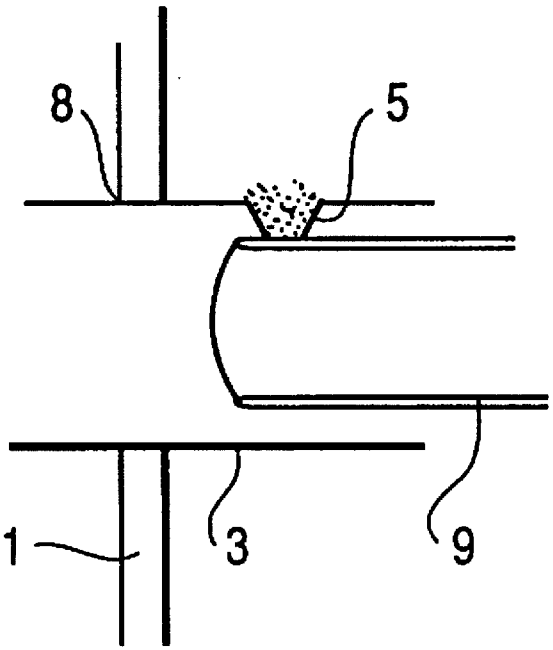

Tests have verified that a device provided with a single dosage recess 5 and sweeper element 4 is capable of reaching a measuring accuracy of appr. ±10% when measuring doses of more than 2 mg. In this case, the medicament container 1 can be half-filled with powder and the measuring accuracy begins to deteriorate after appr. ⅔ of the powder has been spent. Hence, a cylindrical medicament container 1, having a diameter of 2 cm and a height of 1 cm, is capable of measuring or metering more than 200 doses of 2 mg (depending on the specific gravity of a powder in question). Tests have also verified that the flowing characteristics of certain medicinal formulations are insufficient for an accurate operation of the device. This calls for the use of a mechanism which, in a per se known manner, vibrates the medicament container during rotation. The flowing and the filling of a dosage recess can also be intensified by a special design of the interior container wall as well as by adjusting the length and width of a sweeper element and by an eccentric positioning of shaft 5. When measuring doses of less than 2 mg, it is preferable to employ a shaft design as shown in FIG. 3, wherein the shaft 3 is hollow at one end slightly beyond said dosage recess 5. Inside the shaft 3 is fitted a stationary tube 9. After dosage recess 5 has been filled, said shaft 3 is pushed out of container 1 while tube 9 retains its position (FIG. 3b). As some of the gas flow (e.g. induced by inhalation) is directed to pass through said tube 9, the dosage recess is effectively exhausted of medicament.

The medicament container 1 and the gable with its sweeper element 4 for a device of the invention can be readily manufactured from plastics and the components can be joined together e.g. by press-fitting or ultrasonic welding. If the employed material comprises a suitably elastic material, e.g. soft polyethylene or rather stiff elastomer, no separate shaft sealings 8 are not required. A preferred material for the shaft and its inner tube is polished stainless steel.

The filling of a medicinal substance in the container can be effected prior to the attachment of a gable to the container, as one of its shaft apertures is closed, or respectively through the other shaft aperture with the gable in position.

A device of the invention can be replaced in the housing of a powder inhalator either without or with a shaft. If a replacement is effected without a shaft, the shaft apertures of a medicament container are protected for the duration of storage by means of a plug, extending through the medicament container and having one of its ends provided with a depression for receiving the shaft end. After removing an empty container from the shaft, the shaft end is placed in this depression and the container is pushed onto the shaft, which forces the plug in front it out of the container. The container will be installed in its proper position according to alignment marks carried therein as well as in the inhalator housing.

A device of the invention is capable of measuring at a sufficient accuracy both very small and large amounts of powder. The powdered medicament is extremely well protected from moisture and its design readily facilitates the use of a one-way valve for blocking exhalation through the device. It is easy to manufacture and its replaceability guarantees reasonable maintenance costs.

The following description deals with examples for assembling a device of the invention to serve as a complete powder initiator.

FIG. 4a illustrates a simple device, wherein the passage of a dose into an inhalation conduit 10 is effected by manually pressing a button 11. The shaft comprises a massive shaft as shown in FIG. 1, one of its ends leaning against a socket 13 tensioned by a spring 11. The medicament container is tensioned in its position by means of an annular, spring-equipped gear- mechanism 14, which only allows the rotation of the medicament container in a proper direction and also vibrates the medicament container upon the rotation thereof for a smoother flow of powdered medicament. The shaft is chamfered at 15 in order to maintain its proper position. The example discloses the use of a digital dose counter 16 as well as a contact 17. The container is replaceable by unlocking a clamp unit 18, whereby a section including the container disenegages together with its shaft along a line 19 (FIG. 4b) and the more expensive section, including the dose counter, is in permanent service.

When using the device, a medicament container 1 is manually turned through one rotation e.g. according to alignment marks, which is followed by pressing in a button 11 and by inhaling through a mouthpiece 20. Upon releasing, the button returns to its original position, whereby the dosage recess pushes itself inside the medicament container is ready for use again.

FIG. 5 illustrates a more complicated embodiment, wherein a device of the invention is used for measuring relatively small amounts of powder in association with a vortex chamber pulverizing pharmaceutical particles, as disclosed in Finnish Patent application 892956. The device employs a shaft design as illustrated in FIG. 3. The passage of a dose occurs automatically out of the medicament container and the inhalator is well protected against moistening caused by exhalation.

The medicament container has a front cover 2, adapted to serve as the rear wall of a vortex chamber 21. The other gable of the container is provided with two meshings, one 12 being in contact with a gear 24 and the other 23 with a spring 25 mounted on the inhalator housing, the purpose of said spring being to prevent rotation of the container in a wrong direction as well as to vibrate the container during rotation. A shaft 26 carries a reversing wheel 27, a splined cylinder 28 as well as a gear 24 and terminates in a prod 29 for supplying an impulse to a digital dose counter 16. A shaft 3 is fitted with a transfer means 30, one of its ends communicating by way of journalled wheels nearly non-frictionally with the slot of splined cylinder 28 as well as with a rail located below the transfer means and in the bottom section of the inhalator.

When reversing wheel 27 is turned through one rotation, said shaft 3 advances into medicament container 1, said inner tube 9 closes the floor of dosage recess 5, the dosage recess fills up, and shaft 3 passes to its original position out of medicament container 1 into said vortex chamber 21. During inhalation through mouthpiece 20, a flap valve 32 serving as a one-way valve opens and air flows through a vortex-chamber inlet tube 33 into the chamber. A small portion of inhalation air travels through dosage recess 5 along tube 9 for thoroughly removing, together with the intra-chamber vortex, the medicament from the dosage recess.

Exhalation through the device can be done through the dosage recess and tube 9. In practice, however, this is not possible since, when measuring or metering small doses, the hole in the floor of a dosage recess is less than 1 mm in diameter and, thus, a patient does not feel capable of exhaling with a flap valve closing the actual air inlet.

If a massive shaft is employed, exhalation through the device is completely blocked.

The medicament container is replaced by unlocking a hinged portion included in clamp unit 18 and by turning reversing wheel 27 through one rotation. Thus, medicament container 1 comes out as pushed by the shaft, whereby it is easy to pull off of shaft 3. A fresh container is installed in position, as described above (page 9).

Figure 7:
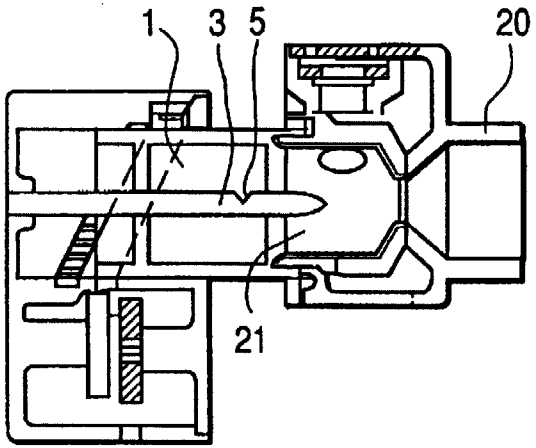
Figure 9B:
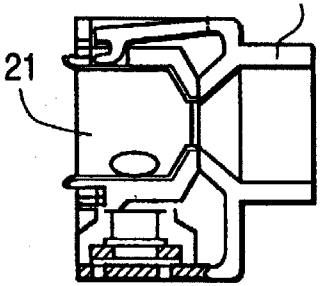
Figure 6:
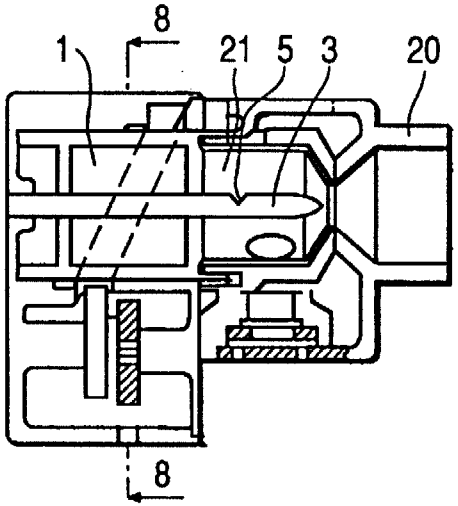
Figure 9A:
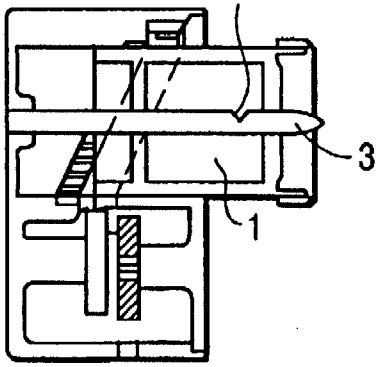
Figure 8:
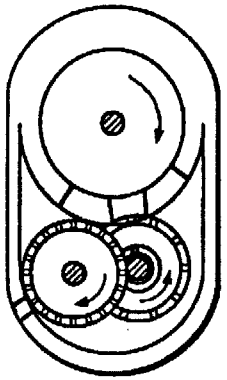

FIGS. 6–9 illustrate one modification to FIG. 5 of an inhalation device provided with a novel metering system. In this modification of an inhalation device, a shaft 3 equipped with a dosage recess 5 remains stationary but, instead, a medicament container 1 and its associated vortex chamber 21 along with its nozzle 20 are movable. A separate section including medicament container 1 is disposed around a fixed shaft 3 provided with dosage recess 5, said shaft penetrating through the medicament container. The open end of the medicament container is provided with a vortex chamber 1 along with its nozzle. A portion of medicament container 1 is provided along its outer wall with a projecting stud, fitting in a spiral slot included in the device. When the device is rotated, the stud travelling in the spiral slot of the medicament container forces medicament container 1 along with its vortex chamber outwards, whereby said medicament container 1 moves and rotates relative to shaft 3. The slot configuration is selected to obtain a complete reciprocating action over a single rotation. In FIG. 6, the device is illustrated in a closed inhalation position, wherein the inhalation recess 5 of shaft 3 is located in vortex chamber 21. In FIG. 7, the device is illustrated at the half-way point of a loading action, wherein said medicament container 1 has displaced outwards relative to shaft 3 in a manner that said dosage recess 5 is now located in medicament container 1. FIG. 8 shows a cross-section along a line A—A in FIG. 6 and FIG. 9 illustrates the device in an opened condition for the replacement of a container for a medicinal substance 1.

I claim:

1. A device intended for measuring a dose of powdered medicament for inhalation, comprising a medicament container (1), through which extends a shaft (3) provided with at least one dosage recess (5), characterized in that said container (1) is provided with at least one flap-shaped sweeper element (4) having opposite ends, resting on shaft (3) in alignment with the dosage recess and having one of its ends rotatable around said shaft (3), the other end of the flap dragging along the shaft surface, said shaft (3) being displaceable in its longitudinal direction relative to said container (1) so as to bring said dosage recess (5) along with its dose of medicament outside said container (1).

2. A device as set forth in claim 1, characterized in that one of the ends of sweeper element (4) is fastened to the wall of container (1), said container being rotatable around shaft (3).

3. A device as set forth in claim 1 or 2, characterized in that said shaft (3) is at least partially hollow.

4. A device as set forth in claim 3, characterized in that said dosage recess (5) is in communication with the hollow section of shaft (3).

5. A device as set forth in claim 3, characterized in that the wall of shaft (3) is provided with a recess (5) opening into the hollow space and that the hollow space includes a stationary tube (9), which extends into medicament container (1) to the proximity of its other wall past recess (5), said shaft (3) being pushable relative to the container and said fixed tube (9) through such a distance that said recess (5) is brought outside container (1).

6. A device as claimed in claim 1, characterized in that said medicament container (1), together with its flap-shaped sweeper element (4) and lead-in sealings (8), is replaceable.

7. A device as claimed in claim 1, characterized in that the device is provided with a limiter for the direction of container rotation, said limiter preventing the rotation of container (1) in a wrong direction.

8. An inhalation apparatus, provided with a device as claimed in claim 1 intended for measuring a dose of powdered medicament for inhalation.

9. An inhalation apparatus as set forth in claim 8, characterized in that it is provided with a one-way valve (32) for preventing exhalation through the apparatus.

*10. A device for measuring a dose of powdered medicament and mixing the dose of powdered medicament with a stream of air for inhalation, the device comprising:*

*a first portion having a shaft secured thereto, the shaft having a dosage recess;*

*a second portion relatively rotatable with respect to the first portion, the second portion including an inhalation chamber having an inlet through which air is drawn connected to an outlet through which a mixture of air and a powdered medicament is inhaled, the second portion also including a powdered medicament container disposed adjacent the inhalation chamber;*

*one of said first and second portions including a projecting stud and the other of said portions including a slot which receives the stud, the slot engaging the stud to move said first and second portions away from each other upon relative rotation of said portions;*

*wherein the shaft is relatively longitudinally displaceable with respect to the medicament container and the inhalation chamber of the second portion along a longitudinal axis of the shaft by relative rotation of said first portion and said second portion, the rotation permitting placement of the shaft dosage recess within the inhalation chamber of said second portion;*

*whereby positioning the dosage recess of the shaft within said medicament container fills the dosage recess with a dose of powdered medicament, and subsequent longitudinal displacement of said shaft with respect to the second portion by relative rotation of said first and second portions positions the filled dosage recess of said shaft within said inhalation chamber to permit inhalation of a mixture of air and powdered medicament by a user.*

*11. A device according to claim 10, wherein the shaft is fixed to said first portion, and said second portion is rotatable around said shaft to move the medicament container and inhalation chamber longitudinally relative said shaft.*

*12. A device according to claim 10, wherein said powdered medicament container is removable from the second portion to facilitate removal and replacement of said container.*

* * * * *